(12) United States Patent
Wang et al.

(10) Patent No.: US 10,342,707 B2
(45) Date of Patent: Jul. 9, 2019

(54) WOUND DRESSING

(71) Applicant: FOSHAN UNITED MEDICAL TECHNOLOGIES, LTD., Foshan (CN)

(72) Inventors: Xiaodong Wang, Foshan (CN); Xiaohui Mo, Foshan (CN); Caixia Feng, Foshan (CN); Jianpeng Xiao, Foshan (CN)

(73) Assignee: FOSHAN UNITED MEDICAL TECHNOLOGIES, LTD., Foshan (CN)

( * ) Notice: Subject to any disclaimer, the term of this patent is extended or adjusted under 35 U.S.C. 154(b) by 418 days.

(21) Appl. No.: 15/191,508

(22) Filed: Jun. 23, 2016

(65) Prior Publication Data

US 2016/0317353 A1 Nov. 3, 2016

Related U.S. Application Data

(63) Continuation-in-part of application No. PCT/CN2014/089318, filed on Oct. 23, 2014.

(30) Foreign Application Priority Data

Dec. 25, 2013 (CN) .......................... 2013 1 0728101

(51) Int. Cl.
*A61F 13/00* (2006.01)
*A61F 13/02* (2006.01)
*A61L 15/26* (2006.01)
*A61L 15/28* (2006.01)
*A61L 15/44* (2006.01)

(52) U.S. Cl.
CPC .. *A61F 13/00029* (2013.01); *A61F 13/00012* (2013.01); *A61F 13/00017* (2013.01); *A61F 13/00042* (2013.01); *A61F 13/00995* (2013.01); *A61F 13/022* (2013.01); *A61F 13/0206* (2013.01); *A61F 13/0213* (2013.01); *A61F 13/0223* (2013.01); *A61L 15/26* (2013.01); *A61L 15/28* (2013.01); *A61L 15/44* (2013.01); *A61L 2300/232* (2013.01); *A61L 2300/404* (2013.01)

(58) Field of Classification Search
None
See application file for complete search history.

(56) References Cited

U.S. PATENT DOCUMENTS

| 3,871,378 | A | * | 3/1975 | Duncan | A61F 13/47245 |
| | | | | | 604/372 |
| 3,901,238 | A | * | 8/1975 | Gellert | A61F 13/15585 |
| | | | | | 604/366 |
| 2012/0220908 | A1 | * | 8/2012 | Evans | A61F 13/041 |
| | | | | | 602/6 |

FOREIGN PATENT DOCUMENTS

CN 103126806 A * 6/2013

* cited by examiner

*Primary Examiner* — Kim M Lewis

(74) *Attorney, Agent, or Firm* — Matthias Scholl P.C.; Matthias Scholl

(57) ABSTRACT

A wound dressing, including: a first outer layer, a second outer layer, and a middle layer disposed between the first outer layer and the second outer layer. The volume density of the first outer layer and a volume density of the second outer layer are greater than that of the middle layer; the first outer layer, the second outer layer, and the middle layer are bonded together.

9 Claims, 2 Drawing Sheets

WOUND DRESSING

CROSS-REFERENCE TO RELATED APPLICATIONS

This application is a continuation-in-part of International Patent Application No. PCT/CN2014/089318 with an international filing date of Oct. 23, 2014, designating the United States, now pending, and further claims priority benefits to Chinese Patent Application No. 201310728101.6 filed Dec. 25, 2013. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

This invention relates to a three-layered wound dressing.

Description of the Related Art

Typical wound dressings are made of two or more kinds of uniformly mixed fibers. Conventionally, the fibers have a fixed bulk density and loose surface structure, so that the water absorption and retention capacity of the wound dressings is poor. When replacing the wound dressings, often stray fibers are left on the wound. Irrigation is often used to remove these fibers. However, this increases the labor load, and may be uncomfortable to the patients.

SUMMARY OF THE INVENTION

In view of the above-described problems, it is one objective of the invention to provide a wound dressing that has high moisture absorption and retention capacity.

To achieve the above objective, in accordance with one embodiment of the invention, there is provided a three-layered fabric that comprises a first layer and a second layer as two outer layers, and a third layer disposed between the first and the second layers.

The volume density of the first and the second layers is greater than that of the middle (third) layer, and the three layers are bonded together. The weight of the first and the second layers is between 8-140 gram per square meter (gsm); the volume density of the first and the second layers is between 0.08-0.32 gram per cubic cm. Preferably, the weight of the first and the second layers is between 10-100 gsm; and the density of the first and the second layers is between 0.08-0.25 g/cm$^3$.

Either the first layer or the second layer or both layers is a fabric containing alginate, or chitosan, or cellulose, or carboxymethyl chitosan, or acylated chitosan, or carboxymethyl cellulose (CMC), or carboxyl ethyl cellulose (CEC), or water insoluble cellulose alkyl sulfonate fiber, or polyvinyl alcohol fiber (PVA), or polypropylene (PP), or polyester (PET), or polyamide (PA), or polyacrylonitrile (PAN).

Either the first layer or the second layer or both layers may contain antimicrobial agent at the concentration of 0.01-25% by weight of the first layer or the second layer, preferably 0.1-20%. The middle layer can also contain antimicrobial agent at the concentration of 0.01-20% by weight of the third (middle) layer, preferably 01-10%. The preferred antimicrobial agent is silver.

Either the first layer or the second layer or both is a knitted fabric, or woven fabric or a nonwoven fabric. The third (middle) layer may be a nonwoven fabric. The knitted or woven fabrics are made from staple yarns or filament. The linear density of the fiber or the filament is between 0.5-10 dtex, preferably 1-6 dtex.

The third (middle) can contain one of the following fibers: alginate, chitosan, cellulose, carboxymethyl chitosan, acylated chitosan, carboxymethyl cellulose (CMC), carboxyl ethyl cellulose (CEC), water insoluble cellulose alkyl sulfonate fiber, bi-component fiber, polyvinyl alcohol fiber (PVA), polypropylene (PP), polyester (PET), Polyamide (PA), Polyacrylonitrile (PAN), cross-linked acrylates copolymer super absorbent fibers (SAF), wood pulp. The middle layer can also be made with a blend of above two or more fibers.

The weight of the middle layer is between 60-600 gsm, preferably 80-500 gsm, more preferably 100-400 gsm.

The fiber linear density of the middle layer is between 0.5-10 dtex, preferably 1-6 dtex. The fiber length of the middle layer is between 3-150 mm, preferably 5-75 mm The nonwoven of these layers can be made by needle punching, hydroentanglement, thermal bonding and chemical bonding.

The above layers can be laminated together by needle punching, or thermal binding, or chemical (adhesive) bonding or ultrasonic welding, or stitch bonding. When the thermal bonding or ultrasonic welding or stitch bonding method is used, one or more patterns can be created during the lamination, such as square, triangle, rectangle, diamond, circle or dot.

The invention also provides an application of the three-layered fabric in the management of chronic wounds or the moisture management.

The invention also provides a method to manufacture the three-layered wound dressing. The method comprises A) providing fibers for the three layers, and measuring parameters of the fibers; B) manufacturing the web for the middle layer; C) converting the web into nonwoven for the third layer; D) laminating the third layer with the first and the second layers; E) processing the laminated fabric such as by cutting, packing and sterilizing into the three-layered wound dressing.

Advantages of the wound dressing of the invention are summarized below:

1. The wound dressing of the invention comprises three layers, i.e. the first layer, the second layer and the third (middle) layer. The middle layer has a smaller volume density than the two outer layers, so it is easier to absorb and retain moisture or wound exudates.

2. The first layer and the second layer have higher density than the middle layer, so that any moisture or fluid that has been absorbed or contained in the middle layer is locked between the two outer layers, preventing the absorbed moisture or exudates from coming out thus preventing possible body infection or wound maceration. This ensures the outer layers still dry after absorption.

3. The wound dressing with such a three-layered structure has a higher wet strength so it can be removed as one piece without any loose residual fibers left behind.

DETAILED DESCRIPTION OF THE EMBODIMENTS

The invention can be illustrated by the following methods or descriptions, in order to fully understand the method and the technology. The scope of the invention is not limited by the after mentioned examples or descriptions.

The method of the manufacturing of the invention can be described as follow, together with FIG. 1-FIG. 4.

Figure 1:
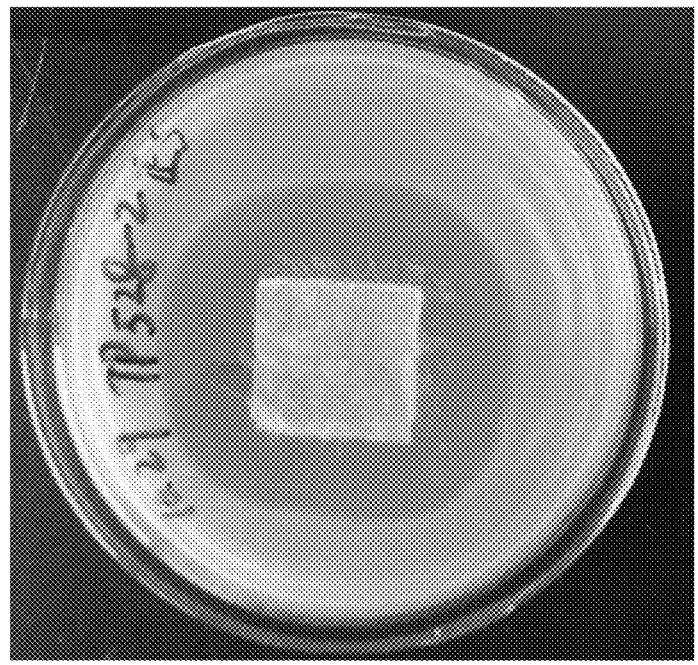
FIG. 1 is an effect picture of the zone of inhibition of a wound dressing in example 2 against *Staphylococcus aureus* at 1 day.
Figure 2:
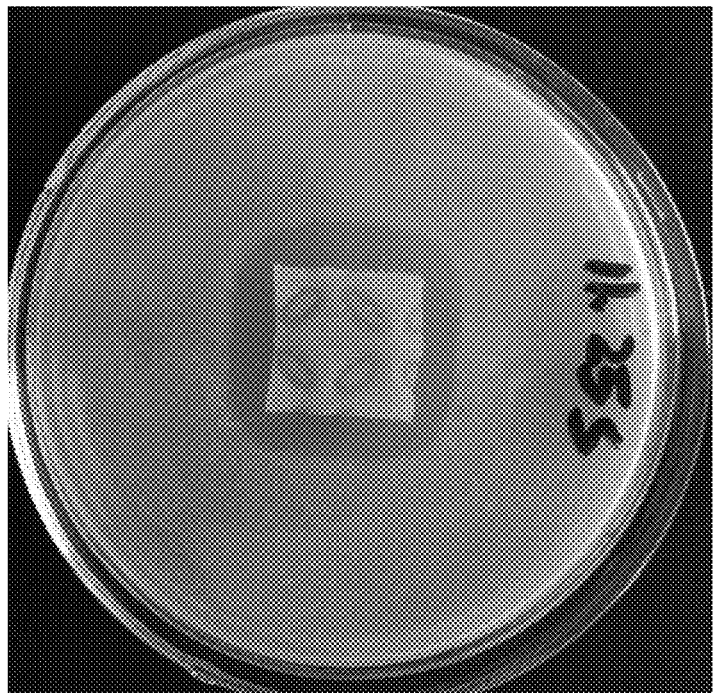
FIG. 2 is an effect picture of the zone of inhibition of a wound dressing in example 5 against *Pseudomonas aeruginosa* at 1 day.
Figure 3:
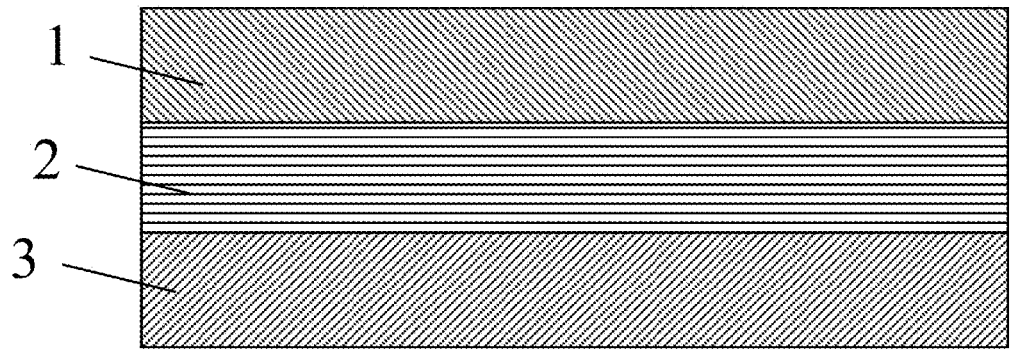
FIG. 3 is a schematic diagram of a three-layered wound dressing of the invention.
Figure 4:
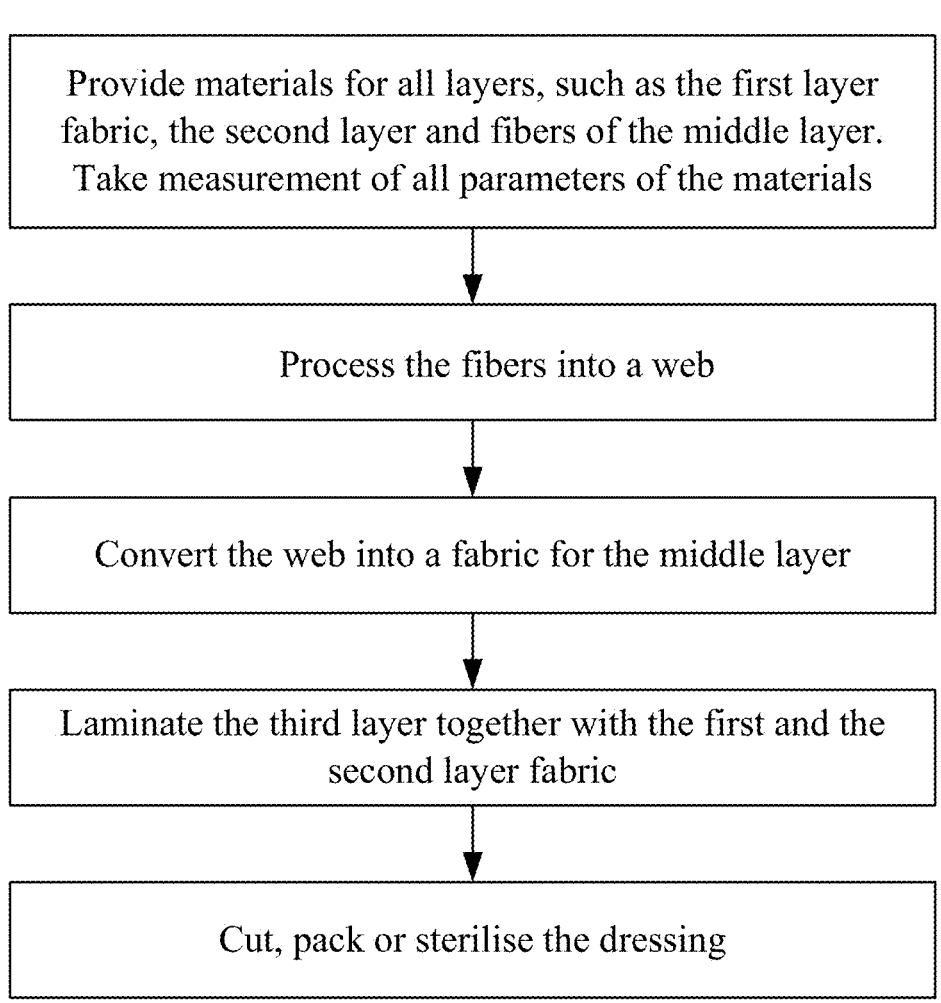
FIG. 4 is a flow chart of a manufacturing method of a three-layered wound dressing of the invention.

The invention provides a three-layered wound dressing, as shown in FIG. 3, comprising a first layer 1, a second layer 3, and a middle (third) layer 2. The first and the second layers are the outer layers of the dressing, the third layer is disposed between the first and the second layers. The volume densities of the first layer and the second layer are greater than that of the middle layer. The three layers are bonded together. The weight of the first layer and the second layer are between 8-140 gsm, preferably 10-100 gsm. The densities of the first layer and the second layer can be between 0.08-0.32 g/cm$^3$, preferably 0.08-0.25 g/cm$^3$. The wound dressing made from this fabric has an absorbency greater than 10 g/100 cm$^2$, and has a sufficient wet strength to allow an intact removal from the wound bed after absorption.

The first layer and/or the second layer can be a fabric of alginate, or chitosan, or cellulose, or chemically modified chitosan, chemically modified cellulose, or PVA, or PP, or PET, or PA or PAN. It can also be made by blending two or more materials from the above mentioned fibers. The first layer and the second layer can be the same fabric or two different fabrics. This means that the fabric of the invention can be symmetric or asymmetric.

The alginate can be a high M alginate, or a high G alginate. It can also be a calcium or calcium/sodium alginate. The chitosan can be a chitosan with a degree of deacetylation of 80% or above. The chemically modified chitosan can be carboxymethyl chitosan or acylated chitosan. The chemically modified chitosan has an absorbency of 500% or above. The cellulose fiber can be traditional viscose fiber or solvent spun cellulose fiber such as lyocell. The chemically modified cellulose can be carboxymethyl cellulose or carboxyl ethyl cellulose, or water insoluble cellulose alkyl sulfonate fiber. The absorbency of the chemically modified fiber is 500% or above.

The first and/or the second layer can have an antimicrobial agent such as silver, PHMB, or honey. The preferred agent is silver, such as silver compound or silver complex. Silver can be applied to the fiber first then made into fabric, or it can be applied directly to the fabric. The silver content can be 0.01-25% by weight of the respective fabric layer, preferably 0.1-20%.

It is not the intention of the invention to limit the method of manufacturing silver fiber/fabric, the following methods can be considered for the application of silver to the fiber or fabric:

1. Add antimicrobial agent such as silver nitrate, silver chloride, silver carbonate, or silver sodium zirconium hydrogen phosphate into the fiber spinning polymer solution (also referred to as dope), then extrude the solution into fibers to make the silver fiber;

2. Spray the silver containing solution to the fiber or fabric surface, such as spray nano silver solution to fiber or fabric surface;

3. Coat silver onto the surface of fiber or fabric.

In addition, either the first layer or the second layer or both can be woven fabric or knitted fabric or nonwoven fabric. The woven fabric is manufactured with a weaving process and equipment. The knitted fabric is manufactured with a knitting process and equipment. The nonwoven fabric is manufactured with a carding and nonwoven process and equipment.

For the woven fabric or knitted fabric, it can be made with staple fiber yarns or filaments, the linear density of the fiber or filament can be between 0.5-10 dtex, preferably 1-6 dtex. For nonwoven fabric, it can be made with needle punching method, or hydroentanglement method, or thermal bonding method, or chemical bonding method. The hydroentanglement method can only be applied to the non-gelling fibers. The thermal bonding method can only be applied to fibers manufactured from the hot melt method.

The middle layer can contain alginate fiber, chitosan fiber, viscose fibers, lyocell fibers, carboxymethyl chitosan fibers, acylated chitosan fibers, carboxymethyl cellulose fibers, carboxyl ethyl cellulose fibers, water insoluble cellulose alkyl sulfonate fibers, bi-component fibers. It can also contain PVA fibers, PP fibers, PET fibers, PA fibers, PAN fibers, cross-linked acrylate copolymer fibers, wood pulp fibers.

The middle layer can also be made by blending two or more following fibers for the wound dressing to have various efficacies: alginate fiber, chitosan fiber, viscose fibers, lyocell fibers, carboxymethyl chitosan fibers, acylated chitosan fibers, carboxymethyl cellulose fibers, carboxyl ethyl cellulose fibers, water insoluble cellulose alkyl sulfonate fibers, bi-component fibers, PVA fibers, PP fibers, PET fibers, PA fibers, PAN fibers, cross-linked acrylate copolymer fibers and wood pulp fibers. For example, by blending alginate and chitosan fiber, it will make the middle layer absorbent and hemostatic. To increase the absorbency, the fabric can be made by bending alginate and carboxymethyl cellulose (CMC) fibers. For improving wet strength, the chemically modified fibers can be mixed with cellulose fiber such as lyocell.

For the wound dressing to have anti-microbial properties, the middle layer can also contain antimicrobial agents such as silver, PHMB or honey, preferably silver, silver compound, or silver complex. The concentration of the antimicrobial agent is 0.01-20%, preferably 0.1-10%.

The weight of the middle layer fabric is 60-600 gsm, preferably 80-500 gsm, more preferably 100-400 gsm.

Staple fibers are used to manufacture the middle layer. The fiber length can be between 3-150 mm, preferably 5-75 mm. The linear density of the fiber is 0.5-10 dtex, preferably 1-6 dtex. The middle layer is a nonwoven fabric manufactured by needle punching method, or thermal bonding method or chemical bonding method.

The three layers of the invention can be laminated together by needle punching, or thermal bonding or ultrasonic welding or chemical (adhesive) bonding or stitch bonding. The needle punching and the chemical bonding are easier to use and can be used for all fibers. Thermal bonding and ultrasonic welding can only be used on fabric which contains hot melt spun fibers. The fabric made from the needle punching method feels soft and the chemically bonded fabric feels rigid. Thermally bonded fabric, the stitch bonded fabric and the fabric made with ultrasonic method can produce some pattern at the bonding points such as square, triangle, rectangle, diamond, circle or dot. These patterns may be used to prevent the lateral spreading of fluid, providing a lateral moisture locking function to the fabric.

The invention also provides a method to manufacture the three-layered fabric or wound dressing:

1) Providing all raw materials i.e. all fibers or filaments for the three layers, and measuring all the parameters of the material;
2) Processing the fibers into a web
3) Converting the web into a fabric for the middle layer;
4) Laminating the third layer together with the first and the second layer fabric;
5) Cutting, packing or sterilizing the wound dressing.

It is also important to describe the measurement of few fabric parameters:

1. Fabric weight

Cut the fabric into square or rectangle, measure the weight G (gram), then place the fabric onto a flat surface to measure its length L (cm) and the width W (cm). The fabric weight can be calculated as follows:

$$Gsm=G\times 100\times 100/(L\times W).$$

2. Fabric thickness or volume density

Place the fabric between the measuring feet of the thickness gauge, the diameter of the measurement feet is 30 mm, pressure 0.5 N. Take the reading of the fabric D (mm) to the nearest 0.001 mm.

Use the thickness and the data in 1) to calculate the volume density P (g/cm$^3$) as follow:

$$P=G\times 10/(L\times W\times D).$$

3. Fiber linear density: Follow the method provided in GB/T 14335 Linear density test method for man-made fibers
4. Fiber length: Follow the method provided in GB/T 14335 Linear density test method for man-made fibers The following examples describe the manufacturing method and the structure of the fabric/dressing.

The solution A referred to in this application is a solution provided in BS EN 13726-2002 which contains 8.298 g/l of sodium chloride and 0.368 g/l of calcium chloride dehydrate and distilled water.

EXAMPLE 1

The first and the second fabric in this example is PP fabric, and the middle layer is Mid M alginate fabric.

The detailed manufacturing steps are as follows:

The first and second layer use spun bond PP nonwoven, weight 12 gsm, volume density 0.08 g/cm$^3$, white in color.

The middle layer contains in-house made MG alginate fibers, linear density 3.0 dtex, fiber length 75 mm, the fiber's absorbency to Solution A is 1400%;

Take 500 g of alginate fibers, open and feed the fibers into a carding machine to form a fibrous web;

Process the web into a needle punched felt as the middle layer fabric, needling density 60/cm$^2$, fabric weight 99 gsm, volume density 0.07 gsm;

Place the above alginate felt between the first and the second fabrics, then feed them together into 2 needle machines respectively. The first machine needles downwards, the second upwards, needling density 100/cm$^2$. This formed the laminated three-layered fabric;

Cut the above laminated fabric into squares 10×10 cm, then pack and sterilize at a dosage of 25-50 KGy;

Test the absorbency of the finished dressing using the YY/T 047.1-2004 and EN 13726-1: 2002/AC:2003 Test Method for Primary Wound Dressing. The results were 19 g/100 cm$^2$.

EXAMPLE 2

The first and the second fabric in this example is PP fabric, the middle layer is Silver CMC fabric (silver carboxymethyl cellulose).

The detailed manufacturing steps are:

The first and second layer use spun bond PP nonwoven, weight 12 gsm, volume density 0.08 g/cm$^3$, white in color.

The middle layer contains in-house made silver carboxymethyl cellulose fibers, linear density 1.7 dtex, fiber length 50 mm, silver content 1%, the fiber's absorbency to Solution A is 1500%;

Take 500 g of silver CMC fibers, open and feed the fibers into a carding machine to make into a fibrous web;

Process the web into a needle punched felt as the middle layer fabric, needling density 60/cm$^2$, fabric weight 130 gsm, volume density 0.078 gsm;

Place the above silver CMC felt between the first and the second fabrics, then feed them together into 2 needle machines respectively. The first machine needles downwards, the second upwards, needling density 100/cm$^2$. This made the laminated three-layered fabric;

Cut the above laminated fabric into 10×10 cm, then pack and sterilize at a dosage of 25-50 KGy;

Test the absorbency of the finished dressing using the YY/T 047.1-2004 and EN 13726-1:2002/AC:2003 Test Method for Primary Wound Dressing. The results were 22 g/100 cm$^2$.

In order to assess the dressing's antimicrobial function, the samples from the above example was cut into a 2×2 cm piece, then placed onto a Petri-dish that has been covered with *Staphylococcus aureus*. The Petri-dish was then placed into an oven at a temperature of 37° C. for 24 hrs, and the growth of the bacteria around the dressing sample on the plate was observed (zone of inhibition). This demonstrates the dressing's ability to kill bacteria after 24 hrs contact time.

EXAMPLE 3

The first and the second fabrics of this example is hydroentanglement Lyocell fabric, the middle layer is a chemically modified chitosan fabric.

The detailed manufacturing steps are:

The first and second layer use hydroentanglement Lyocell nonwoven fabric, weight 30 gsm, volume density 0.13 g/cm$^3$, white in color.

The middle layer contains in-house made acylated chitosan fibers, linear density 2.0 dtex, fiber length 50 mm, the fiber's absorbency to Solution A is 2000%;

Take 500 g of acylated chitosan fibers, open and feed the fibers into a carding machine to make into a fibrous web;

Process the web into a needle punched felt as the middle layer fabric, needling density 40/cm$^2$, fabric weight 125 gsm, volume density 0.075 gsm;

Place the above chitosan felt between the first and the second fabrics, then feed them together into 2 needle machines respectively. The first machine needles downwards, the second upwards, needling density 100/cm$^2$. This made the laminated three-layered fabric;

Cut the above laminated fabric into 10×10 cm, then pack and sterilize at a dosage of 25-50 KGy;

Test the absorbency of the finished dressing using the YY/T 047.1-2004 and EN 13726-1:2002/AC:2003 Test Method for Primary Wound Dressing. The results were 16 g/100 cm$^2$.

EXAMPLE 4

The first and the second fabric in this example is silver nylon (PA) fabric, the middle layer is a chemically modified cellulose fabric.

The detailed manufacturing steps are:

The first and second layer use knitted silver nylon fabric, weight 31 gsm, volume density 0.14 g/cm$^3$, grey in color, silver content 22%.

The middle layer contains in-house made carboxymethyl cellulose fibers, linear density 2.2 dtex, fiber length 50 mm, the fiber's absorbency to Solution A is 2000%;

Take 500 g of CMC fibers, open and feed the fibers into a carding machine to make into a fibrous web;

Process the web into a needle punched felt as the middle layer fabric, needling density 40/cm$^2$, fabric weight 125 gsm, volume density 0.075 gsm;

Place the above CMC felt between the first and the second fabrics, then feed them together into 2 needle machines respectively. The first machine needles downwards, the second upwards, needling density 100/cm$^2$. This made the laminated three-layered fabric;

Cut the above laminated fabric into 10×10 cm, then pack and sterilize at a dosage of 25-50 KGy;

Test the absorbency of the finished dressing using the YY/T 047.1-2004 and EN 13726-1:2002/AC:2003 Test Method for Primary Wound Dressing. The results were 16 g/100 cm$^2$.

EXAMPLE 5

The first and the second fabric in this example is silver nylon (PA) fabric, the middle layer is a chemically modified cellulose fabric. The lamination method is ultrasonic welding.

The detailed manufacturing steps are:

The first and second layer use knitted silver nylon fabric, weight 129 gsm, volume density 0.32 g/cm$^3$, black in color, silver content 25%.

The middle layer contains in-house made carboxymethyl cellulose fibers and the PE/PP di-component fibers (ES-C). The linear density of the CMC fiber is 2.2 dtex, fiber length 50 mm, the fiber's absorbency to Solution A is 2000%; The linear density of the PE/PP fiber is 2.5 dtex, fiber length 45 mm.

Take 500 g of CMC fibers and 100 g of ES fiber, blend evenly, open and feed the fibers into a carding machine to make into a fibrous web;

Process the web into a needle punched felt as the middle layer fabric, needling density 80/cm$^2$, fabric weight 139 gsm, volume density 0.103 gsm;

Place the above CMC felt between the first and the second fabrics, then feed them together into an ultrasonic welding machine to laminate the three layers together. The laminated fabric has a diamond welding pattern;

Cut the above laminated fabric into 10×10 cm, then pack and sterilize at a dosage of 25-50 KGy;

Test the absorbency of the finished dressing using the YY/T 047.1-2004 and EN 13726-1:2002/AC:2003 Test Method for Primary Wound Dressing. The results were 15 g/100 cm$^2$.

In order to assess the dressing's antimicrobial function, the samples from the above example was cut into a 2×2 cm piece, then placed onto a Petri-dish that has been covered with *Pseudomonas aeruginosa*. The Petri-dish was then placed into an oven at a temperature of 37° C. for 24 hrs, and the growth of the bacteria around the dressing sample on the plate was observed (zone of inhibition). This demonstrates the dressing's ability to kill bacteria after 24 hrs contact time.

EXAMPLE 6

The first and the second fabric in this example is asymmetric PP fabric, the middle layer is Mid M alginate fabric (M:G equal ratio).

The detailed manufacturing steps are:

The first layer is a spun bond PP nonwoven, weight 12 gsm, volume density 0.08 g/cm$^3$, white in color. The layer is also a spun bond PP nonwoven, weight 34 gsm, volume density 0.11 g/cm$^3$, orange in color.

The middle layer contains in-house made MG alginate fibers, linear density 3.0 dtex, fiber length 75 mm, the fiber's absorbency to Solution A is 1400%; The middle layer also contains PE/PP di-component fibers (ES-C) with a linear density of 2.5 dtex, fiber length 45 mm Take 1000 g of alginate fibers, blended evenly with the 250 g ES-C fiber, then open and feed the fibers into a carding machine to make into a fibrous web;

Process the web into a needle punched felt as the middle layer fabric, needling density 60/cm$^2$, fabric weight 365 gsm, volume density 0.065 gsm;

Place the above alginate felt between the first and the second fabrics, then place the fabrics together into an oven at 140° C. for 2 minutes, making the ES-C fiber melt and bind together. At the exit of the oven there is a pair of hot rollers (surface temperature 140° C.), the roller surface has a dot-pattern which further laminate the three layer and creates a dot pattern to the laminated fabric. The top of the fabric is white, bottom is orange.

Cut the above laminated fabric into 10×10 cm, then pack and sterilize at a dosage of 25-50 KGy;

Test the absorbency of the finished dressing using the YY/T 047.1-2004 and EN 13726-1:2002/AC:2003 Test Method for Primary Wound Dressing. The results were 14 g/100 cm$^2$.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A wound dressing, comprising: a first outer layer, a second outer layer, and a middle layer disposed between the first outer layer and the second outer layer; wherein
   the volume density of the first outer layer and the volume density of the second outer layer are greater than that of the middle layer;
   the first outer layer, the second outer layer, and the middle layer are bonded together; and weights of the first outer layer and second outer layer are between 8 and 140 grams per square meter (gsm), and volume densities of the first outer layer and the second outer layer are between 0.08 and 0.32 g/cm$^3$.

2. The wound dressing of claim 1, wherein the first outer layer and the second outer layer comprise at least one of the following fibers: alginate, chitosan, cellulose, carboxymethyl chistosan, acylated chitosan, carboxymethyl cellulose, carboxyethyl cellulose, water insoluable cellulose, alkyl sulfonate, polyvinyl alcohol fiber, polypropylene, polyester, polyamide, or polyacrylonitrile.

3. The wound dressing of claim 2, wherein at least one of the first outer layer and second outer layer comprises one antimicrobial agent, and a concentration of the antimicrobial agent is between 0.01% -25% by weight of a corresponding layer; the middle layer comprises the antimicrobial agent, the concentration of the antimicrobial agent is between 0.01%-20% by weight of the middle layer.

4. The wound dressing of claim 3, wherein the antimicrobial agent is silver.

5. The wound dressing of claim 2, wherein at least one of the first outer layer and the second outer layer is a knitted fabric, a woven fabric, or a nonwoven fabric; the middle layer is a nonwoven fabric; the knitted fabric and the woven fabric are made from staple fiber yarn or filament; a linear density of the staple fiber yarn or the filament is between 0.5-10 dtex.

6. The wound dressing of claim 5, wherein the nonwoven fabric is made by needle punching, hydroentanglement, thermal bonding, or chemical bonding.

7. The wound dressing of claim 2, wherein the first outer layer, the second outer layer and the middle layer are laminated together by needle punching or thermal bonding or chemical bonding or ultrasonic welding or stitch bonding; the thermal bonding, stitch bonding and ultrasonic welding are adapted to produce patterns comprising square, triangle, rectangle, diamond, circle and dot.

8. The wound dressing of claim 1, wherein the middle layer comprises at least one of the following fibers: alginate, chitosan, cellulose, carboxymethyl chitosan, acylated chitosan, carboxymethyl cellulose, carboxyethyl cellulose, water insoluble cellulose alkyl sulfonate fiber, bi-component fiber, polyvinyl alcohol, polypropylene, polyester, polyamide, polyacrylonitrile, cross-linked acrylates copolymer super absorbent fibers, and wood pulp.

9. The wound dressing of claim 8, wherein the weight of the middle layer is between 60-600 gsm; a fiber linear density of the middle layer is between 0.5-10 dtex; and a fiber length thereof is between 3-150 mm.

\* \* \* \* \*